United States Patent [19]

Adams et al.

[11] 4,367,338

[45] Jan. 4, 1983

[54] URAZOLE ANALOGS OF PROSTAGLANDINS

[75] Inventors: David R. Adams, Epping; Alexander C. Goudie, Harlow, both of England

[73] Assignee: Beecham Group Limited, England

[21] Appl. No.: 858,554

[22] Filed: Dec. 8, 1977

[30] Foreign Application Priority Data

Dec. 18, 1976 [GB] United Kingdom ............... 52956/76
Oct. 19, 1977 [GB] United Kingdom ............... 43407/77

[51] Int. Cl.³ .................... A61K 31/41; C07D 249/12
[52] U.S. Cl. .................................. 548/264; 424/269; 542/426; 542/427; 560/157
[58] Field of Search .................... 260/308 R, 308 C; 542/413, 426; 424/269

[56] References Cited

U.S. PATENT DOCUMENTS 4,032,533  6/1977  Scribner ............................. 424/270
4,052,407  10/1977  Ambrus et al. .................... 424/270
4,079,145  3/1978  Reuschling et al. ................ 542/426

OTHER PUBLICATIONS

Kahn et al., Prostaglandins and Cyclic AMP, (Academic Press, 1973), pp. 8-9.
Weeks, Annual Review of Pharmacology, vol. 12, 1972, (Palo Alto, Calif., 1972), p. 317.

*Primary Examiner*—Alton D. Rollins
*Attorney, Agent, or Firm*—Jacobs & Jacobs

[57] ABSTRACT

Compounds of formula (I)

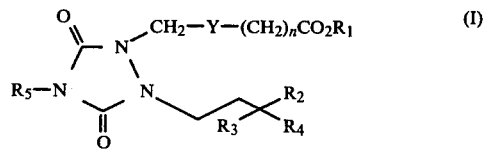

wherein:

n is 1 to 5

Y is —$CH_2$—$CH_2$ or —CH=CH—;

$R_1$ is hydrogen or $CO_2R_1$ represents an ester group in which the $R_1$ moiety contains from 1-12 carbon atoms;

$R_2$ is hydrogen, $C_{1-4}$ alkyl, or phenyl;

$R_3$ is hydroxy or protected hydroxy;

$R_4$ is hydrogen, $C_{1-9}$ alkyl, $C_{3-8}$ cycloalkyl, $C_{3-8}$ cycloalkyl-$C_{1-6}$ alkyl, phenyl, phenyl —$C_{1-6}$ alkyl, naphthyl, naphthyl $C_{1-6}$ alkyl, any of which phenyl moieties or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups;

$R_5$ is hydrogen, $C_{1-6}$ alkyl, $C_{5-8}$ cycloalkyl, phenyl, phenyl-$C_{1-6}$ alkyl or phenyl $C_{3-6}$ cycloalkyl, any of which phenyl moieties may be substituted by one or more halogen, trifluoromethyl, $C_{1-6}$ alkyl, $C_{1-6}$ alkoxy or nitro groups;

or $R_2$ and $R_4$ taken with the carbon atom to which they are joined represent a $C_{5-8}$ cycloalkyl group; and salts thereof are useful for their prostaglandin-like activity.

24 Claims, No Drawings

URAZOLE ANALOGS OF PROSTAGLANDINS

This invention relates to novel compounds having pharmacological activity, to a process for their preparation, to intermediates useful in that process and to pharmaceutical compositions containing them.

Offenlegungsschrift No: 2323193 discloses that pyrazolidine derivatives of the formula (I)':

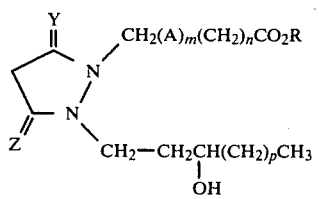

wherein;

A is CH=CH or C≡C; R is H, an alkali metal, an amine salt, or an γ 12C hydrocarbon or chlorohydrocarbon residue; m is 0 or 1; n is 0-6; p is 0-6; and Y and Z are 0 or H except that Y and Z are not both 0; have similar biological properties to the prostaglandins or are antagonists of prostaglandins.

French patent application No: 2258376 discloses that 10-aza prostaglandins of formula (II)'':

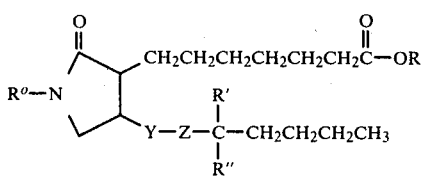

wherein;

R=H or lower alkyl; R' and R''=CH$_3$ or C$_2$H$_5$; R°=H or lower alkyl; Y=—CH$_2$—CH$_2$—, or —CH=CH—; Z=—CO or —CH(~OH)—; are useful in the treatment of blood pressure and gastro-intestinal disorders, and in the preparation for confinement.

Belgian Pat. No: 835989 discloses that compounds of the formula (III)'':

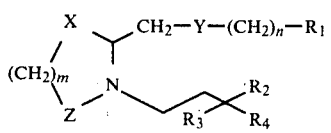

wherein:

X is CO, protected CO, CROH in which R is hydrogen or C$_{1-4}$alkyl and in which the OH moiety may be protected; Y is CH$_2$CH$_2$ or CH=CH; Z is CO or CH$_2$; n is 1 to 8; m is 1, 2 or 3; R$_1$ is hydrogen, CH$_2$OH, CH$_2$OH in which the OH moiety is protected, CO$_2$W wherein W is hydrogen or CO$_2$W represents an ester group in which the ester moiety contains from 1 to 12 carbon atoms, or CONH$_2$; R$_2$ is hydrogen, C$_{1-4}$alkyl, or taken together with R$_3$ and the carbon atom to which it is attached represents a carbonyl group; R$_3$ is hydrogen, hydroxy or protected hydroxy; R$_4$ is hydrogen or C$_{1-9}$alkyl; and salts thereof; have useful pharmacological activity.

A novel class of compounds also having useful pharmacological activity has now been discovered, which compounds are structurally distinct from the prior art referred to above. Accordingly the present invention provides a compound of the formula (I);

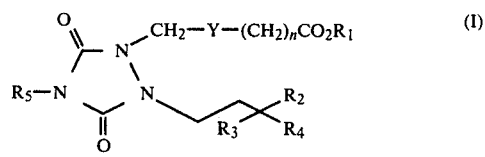

wherein;

n is 1 to 5

Y is —CH$_2$—CH$_2$— or —CH=CH—;

R$_1$ is hydrogen or CO$_2$R$_1$ represents an ester group in which the R$_1$ moiety contains from 1-12 carbon atoms;

R$_2$ is hydrogen, C$_{1-4}$ alkyl, or phenyl;

R$_3$ is hydroxy or protected hydroxy;

R$_4$ is hydrogen, C$_{1-9}$ alkyl, C$_{3-8}$ cycloalkyl, C$_{3-8}$ cycloalkyl-C$_{1-6}$ alkyl, phenyl, phenyl-C$_{1-6}$ alkyl, naphthyl, naphthyl C$_{1-6}$ alkyl, any of which phenyl moieties or naphthyl moieties may be substituted by one or more halogen, trifluoromethyl, C$_{1-6}$ alkyl, hydroxy, C$_{1-6}$ alkoxy, phenyl C$_{1-6}$ alkoxy or nitro groups;

R$_5$ is hydrogen, C$_{1-6}$ alkyl, C$_{5-8}$ cycloalkyl, phenyl, phenyl-C$_{1-6}$ alkyl or phenyl C$_{3-6}$ cycloalkyl, any of which phenyl moieties may be substituted by one or more halogen, trifluoromethyl, C$_{1-6}$ alkyl, C$_{1-6}$ alkoxy or nitro groups;

or

R$_2$ and R$_4$ taken with the carbon atom to which they are joined represent a C$_{5-8}$ cycloalkyl group; and salts thereof.

A group of compounds within formula (I) include those wherein:

n is 1 to 5;

Y is —CH$_2$—CH$_2$ or —CH=CH—;

R$_1$ is hydrogen or CO$_2$R$_1$ represents an ester group in which the R$_1$ moiety contains from 1 to 12 carbon atoms;

R$_2$ is hydrogen, C$_{1-4}$ alkyl, or phenyl;

R$_3$ is hydroxy or protected hydroxy;

R$_4$ is hydrogen, C$_{1-9}$ alkyl, C$_{5-8}$ cycloalkyl, C$_{5-8}$ cycloalkyl-C$_{1-6}$ alkyl, phenyl, phenyl-C$_{1-6}$ alkyl, naphthyl, naphthyl C$_{1-6}$ alkyl, any of which phenyl or naphthyl moieties may be substituted by one or more halogen, trifluoromethyl, C$_{1-6}$alkyl, C$_{1-6}$ alkoxy or nitro groups;

R$_5$ is hydrogen, C$_{1-6}$ alkyl, phenyl or phenyl-C$_{1-6}$ alkyl; and salts thereof.

Suitably n is 2, 3 or 4, preferably 3. Similarly Y may be —CH$_2$—CH$_2$— or —CH=CH—, suitably —CH$_2$—CH$_2$—.

R$_1$ is hydrogen or CO$_2$R$_1$ represents an ester group in which the R$_1$ moiety contains from 1 to 12 carbon atoms. Examples of R$_1$ include hydrogen, methyl, ethyl, n- and iso-propyl, n-, sec- and tert-butyl, phenyl, benzyl, toluyl and the like, while normally hydrogen or C$_{1-6}$ alkyl groups are preferred.

Suitable examples of R$_2$ include hydrogen; methyl, ethyl; and phenyl. Preferred examples of R$_2$ include hydrogen.

Suitable protected hydroxy groups R$_3$ include readily hydrolysable derivatives such as acylated hydroxy groups in which the acyl moiety contains 1 to 4 carbon atoms, for example the acetoxy group; and hydroxy groups etherified by readily removable inert groups such as the benzyl or like groups. Preferably however R$_3$ is hydroxy.

Suitable groups R$_4$ when R$_4$ is an alkyl group include C$_{4-9}$ alkyl groups. Such C$_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example, R$_4$ may be a group CH$_2$R$_6$, CH(CH$_3$)R$_6$ or C(CH$_3$)$_2$R$_6$, wherein R$_6$ is a straight chain alkyl group such that the carbon content of the resultant group R$_4$ is 4 to 9.

In general preferred groups R$_4$ when R$_4$ is an alkyl group include straight chain pentyl, hexyl, and heptyl groups. Other preferred groups R$_4$ include groups CH(CH$_3$)$R_6$ and C(CH$_3$)$_2$R$_6$ wherein R$_6$ is straight chain butyl, pentyl and hexyl.

When R$_4$ is or contains a C$_{3-8}$ cycloalkyl moiety, the moiety may suitably be a C$_{5-8}$ cycloalkyl moiety such as a cyclohexyl moiety. It may be a cyclopropyl moiety. Examples of suitable C$_{1-6}$ alkyl moieties when R$_4$ is a cycloalkyl-C$_{1-6}$ alkyl group include methyl, ethyl, propyl, butyl and amyl.

When R$_2$ and R$_4$ together with the carbon atom to which they are joined represent a C$_{5-8}$ cycloalkyl group, they suitably represent cyclohexyl.

When R$_4$ is an aryl group as previously defined, suitable groups R$_4$ include phenyl, phenylmethyl, phenylethyl, phenyl n-propyl, phenyl-n-butyl, naphthyl, naphthylmethyl, naphthylethyl, naphthyl n-propyl and naphthyl n-butyl, and such groups branched in the alkyl moiety by one or two methyl groups (at the same or different carbon atoms). These groups may be substituted in the phenyl or naphthyl moiety by normally one, two or three groups selected from those substituent groups listed hereinbefore. Examples of suitable substituent groups include fluorine, chlorine and bromine atoms and CF$_3$, methyl, ethyl n-and iso-propyl, methoxy, ethoxy, n- and iso-propoxy and nitro groups. Other examples of such groups include hydroxy and benzyloxy. Preferably the aryl moieties when substituted by such groups will be mono- or di-substituted.

Suitable examples of R$_5$ include hydrogen; methyl, ethyl, n- and iso-propyl, and n-, sec- and tert-butyl; phenyl; phenylmethyl, phenylethyl, phenyl-n-propyl and phenyl-n-butyl, and such groups branched in the alkyl moiety by one or two methyl groups (at the same or different carbon atoms). Preferred R$_5$ groups include C$_{1-6}$ alkyl.

Other examples of R$_5$ include cyclohexyl; and the aforementioned R$_5$ phenyl containing groups in which the phenyl moieties are substituted as for R$_4$ aryl groups.

R$_5$ may also be a phenyl-C$_{3-6}$ cycloalkyl group, in which case suitable examples of R$_5$ include phenylcyclopropyl.

The compounds of the formula (I) may form conventional salts when R$_1$ is hydrogen and also when R$_5$ is hydrogen.

Such salts include those with alkali and alkaline earth metals, suitably sodium and potassium, and ammonium and substituted ammonium salts.

Normally salts of the R$_5$ hydrogen will be with alkali metals. One particularly suitable sub-group of compounds within formula (I) is of formula (II):

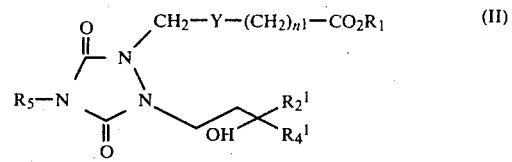

wherein:
Y, R$_1$ and R$_5$ are as defined in formula (I);
n$^1$ is 2, 3 or 4;
R$^1_2$ is hydrogen, methyl, ethyl or phenyl;
R$^1_4$ is hydrogen or C$_{1-9}$ alkyl; and salts thereof.

Suitably in formula (II) n$^1$ is 3.

Suitably R$_1$ is hydrogen or C$_{1-6}$alkyl, preferably hydrogen.

Suitably R$^1_2$ is hydrogen, methyl or ethyl.

While R$_4$ may be hydrogen or a C$_{1-9}$ alkyl group in formula (II), it is normally a C$_{4-9}$ alkyl group. In such cases suitable and preferred straight chain and branched groups R$^1_4$ include those previously described as suitable and preferred for the group R$_4$ when R$_4$ is a C$_{4-9}$ alkyl group. Such preferred groups R$^1_4$ include straight chain pentyl, hexyl and heptyl. Other preferred groups R$^1_4$ include CH(CH$_3$)R$^1_6$ and C(CH$_3$)$_2$R$^1_6$ wherein R$^1_6$ is straight chain butyl, pentyl or hexyl.

Often in formula (II) R$_5$ will be a C$_{1-6}$alkyl, phenyl or phenyl C$_{1-6}$ alkyl group, or hydrogen.

Preferably R$_5$ is a C$_{1-6}$ alkyl group.

From the aforesaid it will be realised that one preferred group within formula (II) is of formula (III):

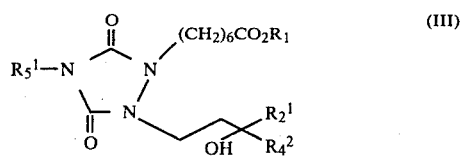

wherein:
R$_1$ is as defined in formula (I);
R$^1_2$ is hydrogen, methyl or ethyl;
R$^2_4$ is a C$_{4-9}$ alkyl group;
R$^1_5$ is a C$_{1-6}$ alkyl group; and salts thereof.

Suitably R$_1$ in formula (III) is hydrogen or C$_{1-6}$alkyl, preferably hydrogen. Suitable and preferred groups R$^2_4$ include those listed hereinbefore for R$^1_4$ when R$^1_4$ is a C$_{4-9}$ alkyl group.

Preferred groups R$^1_5$ include methyl.

Another particularly suitable sub-group of compounds within formula (I) is of formula (IV):

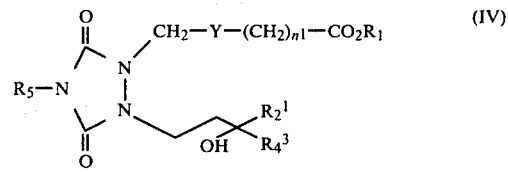

wherein:
Y, R$_1$, and R$_5$ are as defined in formula (I);
n$^1$ is 2, 3 or 4;
R$^1_2$ is hydrogen, methyl, ethyl or phenyl;
R$^3_4$ is a group of formula (V):

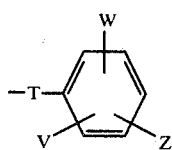
(V)

wherein;

T is a bond, or a $C_{1-6}$ alkylene group which may be straight chain or branched by one or two methyl groups at the same or different carbon atoms; and V, W and Z are each hydrogen or fluorine, chlorine or bromine atoms, or $CF_3$, methyl, ethyl, n- or iso-propyl, methoxy, ethoxy, n or iso-propoxy or nitro groups; and salts thereof.

In formula (IV) it is preferred that $n^1$ is 3.

Suitably $R_1$ is hydrogen or $C_{1-6}$ alkyl, more preferably hydrogen.

In formula (V) it is often preferred that T is a group $-(CH_2)_q-$ wherein q is 0 to 4. Also V and W will often be hydrogen.

Often in formula (II) $R_5$ will be a $C_{1-6}$ alkyl, phenyl or phenyl $C_{1-6}$ alkyl group, or hydrogen.

Preferably $R_5$ is a $C_{1-6}$ alkyl group, such as methyl.

A further sub-group of compounds within the formula (I) is of formula (VI):

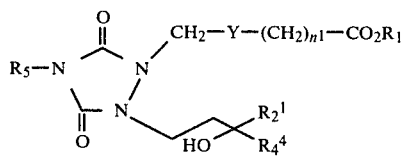

wherein the variable groups are as defined in formula (II) and $R^4_4$ is a group of formula (VII):

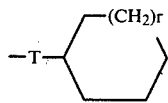

wherein T is as defined in formula (V) and r is 0–3.

Suitable and preferred variable groups in formula (VI) are as in formula (II).

T will often be of a group $-(CH_2)_q-$ wherein q is 0 to 4. Also suitably r is 1.

One compound of the invention that is particularly preferred for its useful activity is compound 32 of Table 6 of the Examples.

The invention also provides a process for the preparation of a compound of the formula (I), which process comprises reacting a compound of formula (IX):

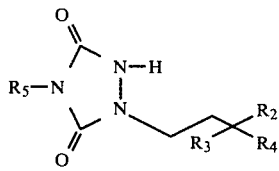

wherein;

$R_2$, $R_3$, $R_4$ and $R_5$ are as defined in formula (I), with a compound of formula (X): $Z-CH_2-Y-(CH_2)_n CO_2R_1$ wherein Z is a good leaving group, and Y, n and $R_1$ are as defined in formula (I).

Z is suitably a halogen, such as bromine, and the reaction suitably carried out in an organic solvent such as hexamethylphosphoramide or the like in the presence of a base such as sodium carbonate or the like. Generally it is preferred that $R_1$ in the compound of formula (X) is other than hydrogen, and so if in this case a $R_1$ hydrogen compound of the formula (I) is desired it is prepared from the thus formed compound of the formula (I) by a conventional de-esterification reaction. When $R_3$ is a protected hydroxy group in the compound of formula (IX), then if in this case a compound of the formula (I) wherein $R_3$ is hydroxy is required it is prepared from the thus formed $R_3$ protected hydroxy compound by conventional de-protection reactions. For example, when $R_3$ is a benzyloxy group, the benzyl group may readily be removed by hydrogenolysis. Thus it can be seen that compounds of the formula (I) wherein $R_3$ is protected hydroxy are useful intermediates in the preparation of the corresponding free hydroxy compounds of the formula (I).

The invention also provides a preferred process for the preparation of a compound of the formula (I), which process comprises reacting a compound of the formula (XI):

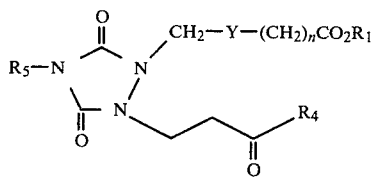

wherein;

Y, n, $R_1$, $R_4$ and $R_5$ are as defined in formula (I); with a reducing agent to give a corresponding compound of the formula (I) wherein $R_2$ is hydrogen and $R_3$ is hydroxy, or with a $C_{1-4}$ alkyl or phenyl Grignard reagent or $C_{1-4}$ alkyl or phenyl metallic complex to give a corresponding compound of the formula (I) wherein;

$R_2$ is $C_{1-4}$ alkyl or phenyl, and $R_3$ is hydroxy; and then optionally protecting the $R_3$ hydroxy moiety.

The reduction of the side chain carbonyl in a compound of the formula (XI) may be carried out by conventional methods for reducing a ketone to an alcohol, for example by sodium borohydride reduction.

The $C_{1-4}$ alkyl or phenyl Grignard reagent or $C_{1-4}$ alkyl or phenyl metallic (suitably $C_{1-4}$ alkyl or phenyl lithium) complex reaction may be carried out under conventional conditions for such reactions, for example in an inert anhydrous solvent.

The optional protection of the $R_3$ hydroxy moiety may be carried out in conventional manner, for example by acylating, alkylating or benzylating the $R_3$ hydroxy compound.

After these reactions if so desired the group $R_1$ in the thus formed compounds of the formula (I) may be varied by conventional esterification and/or de-esterification reactions. Similarly when $R_1$ and/or $R_5$ is hydrogen in such compounds of the formula (I), salts of these compounds may be prepared in conventional manner, for example, by reacting the chosen compound of the formula (I) with the required base. Preferably strong bases such as sodium in an alcohol, e.g. ethanol, and similar reagents are used to obtain salts of $R_5$=H compounds.

The preparation of the intermediates for use in the processes of the invention will now be described.

Compounds of the formula (IX) may be prepared by reacting a compound of the formula (XII):

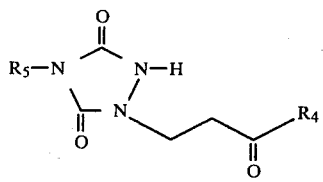
(XII)

with a reducing agent to give a corresponding compound of the formula (IX) wherein $R_2$ is hydrogen and $R_3$ is hydroxy; or by reacting a compound of formula (XIII) as hereinafter defined with a compound of formula (XVI) as hereinafter defined.

The reduction may be carried out as hereinbefore described with reference to compounds of the formula (XI). The reaction of a compound of formula (XIII) with a compound of formula (XVI) may suitably be carried out.

Compounds of the formula (X) are either known compounds or may be prepared by a process analogous to those used for preparing known compounds.

Compounds of the formula (XI) may be prepared by a process which comprises reacting a compound of the formula (XII) as defined with a compound of the formula (X) as defined.

Compounds of the formula (XII) may be prepared by reacting a compound of formula (XIII):

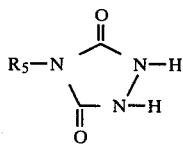
(XIII)

with a strong base and a compound of formula (XIV):

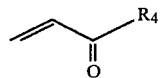
(XIV)

Compounds of the formula (XIII) are either known compounds or can be prepared in analogous manner to known compounds.

For example in our hands, one suitable reaction scheme for the preparation of these compounds is shown Flow Diagram A.

The invention also provides a further preferred process for the preparation of a compound of the formula (I), which process comprises reacting a compound of formula (XV):

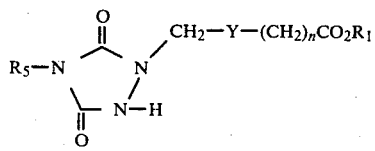
(XV)

wherein;
Y, n, $R_1$ and $R_5$ are as defined in formula (I), with a compound of formula (XVI):

(XVI)

wherein D is a good leaving group, and $R_2$, $R_3$ and $R_4$ are as defined in formula (I).

This reaction is suitably carried out in an inert organic solvent, such as hexamethylphosphoramide or N,N-dimethylformamide, at room temperature, in the presence of a base, such as sodium carbonate or sodium hydride, and a source of alkali metal ions, such as an alkali metal halide. Suitable alkali halides include sodium iodide and lithium iodide.

Suitable examples of D include tosylate, bromide or iodide.

Preferably D is a tosylate residue.

The compound of formula (XV) may be prepared by reacting a compound of formula (XVII):

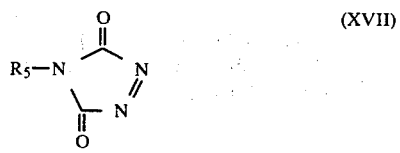
(XVII)

with a compound of formula

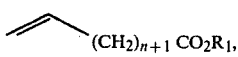
$(CH_2)_{n+1} CO_2R_1$, and then if necessary reducing the resulting Y is CH=CH compound to the corresponding Y is $CH_2CH_2$ compound.

This reaction is suitably carried out in an inert organic solvent, such as benzene, at the reflux temperature, under an inert atmosphere. It should be mentioned that to prepare a compound of the formula (XV) wherein $R_1$ is other than hydrogen, it is generally preferred to prepare the corresponding compound of the formula (XV) wherein $R_1$ is hydrogen and then to convert that compound to the desired compound by conventional methods. For example a $R_1$ is hydrogen compound may be converted to a $R_1$ is methyl compound by treatment with acetyl chloride in methanol.

The optional reduction can be carried out in conventional manner.

The compound of formula (XVII) may be prepared by treating a compound of formula (XIII) as hereinbefore defined, that is, a compound of formula:

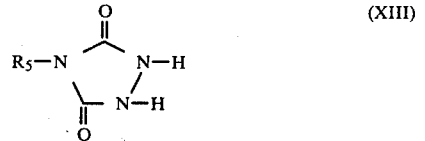
(XIII)

with an oxidising agent, such as $N_2O_4$ or t-butyl hypochlorite.

This reaction is suitably carried out by suspending the chosen compound of the formula (XIII) in an inert organic solvent, such as dichloromethane, at 0° C., and bubbling $N_2O_4$ through this suspension, or adding a known volume of $N_2O_4$ in dichloromethane slowly to the suspension.

The preparation of the compounds of the formula (XIII) has been discussed hereinbefore.

It is believed that compounds of formula (IX), (XI), (XII) and (XV) are novel compounds, and these compounds are useful intermediates as hereinbefore described. As such, they from an important part of this invention.

It will be realised by the skilled reader that although the reaction sequences leading to the active compounds of the invention hereinbefore described are particularly suitable, a number of variations in the sequences are possible. It is believed these variations are best illustrated by use of Flow Diagram B, the reactions represented by arrows being carried out as hereinbefore described or in an analogous manner.

It will of course be realised that the compounds of the formula (I) have an asymmetric centre, and thus are capable of existing in two enantiomeric forms. The invention extends to each of these isomeric forms, and to mixtures thereof. The different isomeric forms may be resolved by the usual methods.

Compounds within the formula (I) have useful pharmacological activity. For example compounds within the formula (I) have anti-gastric secretion activity e.g. anti-ulcer activity, cardiovascular activity e.g. anti-hypertensive activity or anti-arrhythmic activity, platelet aggregation inhibition activity, affect the respiratory tract e.g. bronchodilator activity, and have anti-fertility and smooth muscle activity.

In general it may be said that compounds within the formula (I) have a range of pharmacological activities similar to those shown by the natural prostaglandins, but that these activities tend to be rather more selective.

The invention therefore also provides a pharmaceutical composition comprising a compound of the formula (I) and a pharmaceutically acceptable carrier.

Clearly the formulation of the said pharmaceutical composition will depend on the nature of the activity shown by the chosen compound of the formula (I), and on other factors such as a preference in a particular area of therapy for a particular mode of administration.

The compositions may be in the form of tablets, capsules, powders, granules, lozenges or liquid preparations, such as oral or sterile parenteral solutions or suspensions.

Tablets and capsules for oral administration may be in unit dose presentation from, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, emulsifying agents, nonaqueous vehicles (which may include edible oils), preservatives, and if desired conventional flavouring or colouring agents, and the like.

For parenteral administration, fluid unit dosage forms are prepared utilizing the compound of the formula (I) and a sterile vehicle. The compound, depending on the vehicle and concentration used, can be either suspended or dissolved in the vehicle. In preparing solutions the compound can be dissolved for injection and filter sterilized before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or prophylaxis of disorders in human beings which comprises the administration to the sufferer of an effective amount of a compound of the formula (I).

Animals may also be treated with the compounds of the invention.

Examples 1 to 9 illustrate the preparation of the active compounds of the invention by the (XIII)→(XII)→(XI)→(I) route, as illustrated in the flow diagram.

EXAMPLE 1

Preparation of ethyl-N-tricarboxylate

Ref. Org. Syn. Coll. Vol. III, p. 415, C. F. H. Allen and Alan Bell.

Sodium (44 g, 1.93 g atom) was cut into small pieces and added to a solution of urethane (90 g, 1.01 mol) in dry ether (1.5 l) [the urethane was dried overnight in vacuo over KOH]. The mixture was stirred for 2 hours, then boiled at reflux for 3 hours and then cooled in ice-water. Ethyl chloroformate (210 g, 1.95 mol) was then added dropwise over 2 hours and the resultant mixture stirred overnight at room temperature and then filtered. The residue was washed with ether (2×200 ml) and the ether was removed from the filtrate by evaporation in vacuo. The residual oil was distilled b.p. 118–128/6 mm. Yield 86 g.

EXAMPLE 2

Preparation of ethyl carbazate

C. F. H. Allen and Alan Bell. Org. Syn. Coll. Vol. III, p. 404.

To ethyl-N-tricarboxylate (86 g, 0.37 mol) stirred and cooled in an ice-bath was added slowly hydrazine hydrate (50 g, 1.0 mol). After complete addition the mixture was heated on a water bath for 0.5 hr and to the reaction mixture ethanol (100 ml) was added. This mixture was heated on the water bath (with stirring) for a further 2 hr and then cooled and filtered. The residue was washed with ethanol and the filtrate evaporated in vacuo to give an oil to which more ethanol was added and the solution was allowed to stand overnight at room temperature. The resultant mixture was refiltered, the ethanol was removed from the filtrate in vacuo and the residual oil distilled, b.p. 64°–66°/3 mm. Yield 68 g. This distillate was re-distilled, b.p. 92°–95°/15 mm. Yield 60 g.

EXAMPLE 3

4-Methyl-1,2,4-triazolidine-3,5-dione (Compound 2)

G. Zimmer and W. Deucker. Arch. Pharm., 1961, 294, 370 C. A. 1961, 55, 22298

Ethyl carbazate (12.0 g, 0.115 mol) in dry benzene (60 ml) was treated dropwise with methyl isocyanate (6.5 ml, 6.0 g, 0.105 mol) and after complete addition the mixture was boiled at reflux for 20 min. This solution was allowed to cool and then 4 N aqueous potassium hydroxide (50 ml) was added and the resultant mixture heated at ca. 40° C. for 20 min. This solution was then cooled and acidified with concentrated hydrochloric acid and then evaporated in vacuo to give a white solid. This solid was boiled at reflux in ethanol (300 ml) for 2 hr and the resultant mixture filtered while hot. The filtrate was allowed to cool and refiltered, this filtrate was evaporated to dryness to afford 4-methyl urazole (10.5 g), m.p. 222°–4°. The compounds in Table 1 were prepared in similar manner.

TABLE 1

| Compound | $R_5$ | m.p. |
| --- | --- | --- |
| 1 | Ph | 204–6° |
| 2 | Me | 222–4° |
| 3 | Et | 184–6° |

$R_5$=H (4), available commercially

EXAMPLE 4

4-Methyl-2-(3′-oxo-octyl)-1,2,4-triazolidine-3,5-dione (Compound 7)

To a solution of 4-methyl-1,2,4-triazolidine-3,5-dione (5.75 g, 0.05 mol) in dry dimethylformamide (40 ml) stirred at 75° under a nitrogen atmosphere was added portionwise sodium hydride (1.575 g, 0.055 mol, as an 80% dispersion in mineral oil) and the resultant solution stirred at 75° for 0.5 hr. To this solution was added oct-1-en-3-one (6.57 g, 0.055 mol) dropwise in dimethylformamide (20 ml) and the solution heated with stirring for 48 hr at 75°. The reaction mixture was then cooled, taken up in ethyl acetate (100 ml) and poured into ice-cold 5 N aqueous hydrochloric acid (200 ml). The aqueous layer was separated and extracted with ethyl acetate (4×100 ml). The combined extracts were washed with 5 N aqueous hydrochloric acid, water and then brine, then dried (Na$_2$SO$_4$), filtered and the solvent removed by evaporation in vacuo, to leave a gum (6.55 g). This was chromatographed on silica gel (Merck, Kieselgel 60) with a packing ratio of 1:20 with chloroform as eluant, to afford the triazolidine-3,5-dione (4.61 g) as a gum, which later solidified. (In subsequent preparations the crude material from the reaction mixture could be triturated with hexane to induced crystallisation), m.p. 76°–8°.

The compounds shown in Table 2 were prepared in a similar manner.

TABLE 2

| Compound | $R_5$ | $R_4$ | m.p. °C. |
| --- | --- | --- | --- |
| 5 | H | $C_5H_{11}$ | 91–2 |
| 6 | Ph | $C_5H_{11}$ | 109–111 |
| 7 | Me | $C_5H_{11}$ | 76–78 |
| 8 | Et | $C_6H_{13}$ | 50–52 |
| 9 | Et | $C_5H_{11}$ | GUM |
| 11 | Me | $C_6H_{13}$ | 75–77 |

EXAMPLE 5

1-(6′-Ethoxycarbonyl-n-hexyl)-4-methyl-2-(3″-oxo-n-octyl)-1,2,4-triazolidine-3,5-dione (Compound 14)

4-Methyl-2-(3′-oxo-n-octyl)-1,2,4-triazolidine-3,5-dione (4.0 g, 0.017 mol) was dissolved in hexamethylphosphoramide (60 ml) and sodium carbonate (5.0 g, 0.04 mol), sodium iodide (0.5 g) and ethyl 6-bromoheptanoate (4.327 g, 0.018 mol) in hexamethylphosphoramide (20 ml) were added and the mixture stirred at room temperature for one week. The resultant mixture was poured into water (300 ml), extracted with ethyl acetate (5×100 ml), and the combined extracts washed with water (3×200 ml), brine (2×200 ml), then dried, (Na$_2$SO$_4$) and filtered. The ethyl acetate was removed in vacuo to leave a gum (6.77 g) which was chromatographed on silica gel (Merck, Kieselgel 60), packing ratio 1:20, using chloroform as eluant to afford 1-(6′-ethoxycarbonyl-n-hexyl)-4-methyl-2-(3″-oxo-n-octyl)-1,2,4-triazolidine-3,5-dione (3.56 g) as a gum.

I.r. (cm$^{-1}$): 1770, N—$\overset{O}{\overset{\|}{C}}$—; 1680–1750, —$\overset{O}{\overset{\|}{C}}$—, —N—$\overset{O}{\overset{\|}{C}}$—.

NMR(γ):5.82q, 2H,—CO$_2$CH$_2$CH$_3$;6.15t, NCH$_2$;6.42t, NCH$_2$;6.90s, (CDCl$_3$):N—CH$_3$;7.29t, CH$_2$—$\overset{O}{\overset{\|}{C}}$—,7.65t, $\overset{O}{\overset{\|}{C}}$CH$_2$,—CH$_2$CO$_2$Et.

The compounds listed in Table 3 were prepared in a similar manner.

TABLE 3

| Compound | $R_5$ | $R_1$ | $R_4$ |
| --- | --- | --- | --- |
| 12 | H | Et | $C_5H_{11}$ |
| 13 | Ph | Et | $C_5H_{11}$ |
| 14 | Me | Et | $C_5H_{11}$ |
| 15 | Et | Et | $C_5H_{11}$ |
| 18 | Me | Et | $C_6H_{13}$ |

Compound 12

$R_5$=H, $R_1$=Et, $R_4$=$C_5H_{11}$

I.r.(cm$^{-1}$):1760,—N—C(=O)—;1680-1740,—C(=O)—,N—C(=O)—;—CO$_2$Et

NMR(δ):5.95q,2H,CO$_2$CH$_2$CH$_3$;6.15-6.8 brm,4H,(2 × N—CH$_2$);

(CDCl$_3$) 7.1-8.0 brm, 6H, —CH$_2$—C(=O)—CH$_2$, —CH$_2$CO$_2$Et

Compound 13

R$_5$=Ph, R$_1$=Et, R$_4$=C$_5$H$_{11}$

I.r.(cm$^{-1}$):1775,N—C(=O)—N;1680-1760,N—C(=O)—N,—C(=O)—,CO$_2$Et.

NMR(γ): 2.2-2.9m, 5H, C$_6$H$_5$; 5.92q, 6.1-6.7m, CO$_2$CH$_2$CH$_3$;

(CDCl$_3$):(—N—CH$_2$—)$_2$;7.32t,CH$_2$C(=O)—;7.75t,CCH$_2$;CH$_2$CO$_2$Et.

Compound 18

R$_5$=Me, R$_1$=Et, R$_4$=C$_6$H$_{13}$

I.r. (cm): 1775, —N—C(=O)—; 1660-1740, N—C(=O)—, —C(=O)—; CO$_2$Et,

NMR (γ) (CCl$_4$): 5.95q, CO$_2$CH$_2$CH$_3$, 2H; 6.2-6.8m, (2 × NCH$_2$), 4H;

7.07s, 3H, N—CH$_3$; 7.3-8.0m, 6H, —CH$_2$CO$_2$C$_2$H$_5$, CH$_2$C(=O)—CH$_2$;

8.1-9.3 brm, 22H.

Analysis: Found C, 61.50; H, 9.08; N, 10.27% C$_{21}$H$_{37}$N$_3$O$_5$ requires, C, 61.29; H, 9.06; N, 10.21%.
Mass Spec: Meas. mass 411.2721, Calc. mass 411.2708.

Compound 15

R$_5$=Et, R$_1$=Et, R$_4$=C$_5$H$_{11}$

I.r.(cm$^{-1}$): 1770,—N—C(=O)—;1680-1750,N—C(=O)—, —CO$_2$Et,—C(=O)—.

N.m.r. (60MHz, CDCl$_3$)τ: 5.90q, 2H, —CO$_2$CH$_2$CH$_3$; 6.45 quintet, 6H, (N—CH$_2$)$_3$; 7.1-7.9 m, 6H, CH$_2$CCH$_2$, CH$_2$CO$_2$Et, 8.0-9.3 brm, 23H.

EXAMPLE 6

1-(6'-Ethoxycarbonyl-n-hexyl)-2-(3''-hydroxy-n-octyl)-4-methyl-1,2,4-triazolidine-3,5-dione (Compound 21)

1-(6'-ethoxycarbonyl-n-hexyl)-2-(3''-oxo-n-octyl)-4-methyl-1,2,4-triazolidine-3,5-dione (3.56 g, 9 m mol) was dissolved in dry ethanol (60 ml) and sodium borohydride (0.375 g, 10 m mol) was added portionwise. After stirring at room temperature for 18 hr the ethanol was removed in vacuo, the residue dissolved in water (100 ml) and acidified with 5 N aqueous hydrochloric acid. This aqueous mixture was extracted with ethyl acetate (4×100 ml) and the combined extracts washed with brine (2×100 ml), then dried (Na$_2$SO$_4$), filtered and the solvent removed in vacuo, to leave a gum (3.26 g). This gum was chromatographed on silica gel (Merck, Kieselgel 60) with a packing ratio of 1:30 using benzene and benzene:ethyl acetate mixtures as eluant, to afford 1-(6'-ethoxycarbonyl-n-hexyl)-2-(3''-hydroxy-n-octyl)-4-methyl-1,2,4-triazolidine-3,5-dione (0.94 g) as a gum.

Mass. Spec: Meas. mass 399.2733, calc. mass 399.2733.

I.r. (cm$^{-1}$): 3500, —OH; 1760, N—C(=O)—;

1680-1730, N—C(=O)—, CO$_2$Et.

NMR (τ): 5.81q, CO$_2$CH$_2$CH$_3$, 2H; 6.0-6.1 brm, 5H, (2×N—CH$_2$), CH—OH; (CDCl$_3$) 6.88s, 3H, —N—CH$_3$; 7.30 brs, 1H, —OH; 7.65 brt, —CH$_2$CO$_2$Et.

The compounds listed in Table 4 were prepared in a similar manner.

TABLE 4

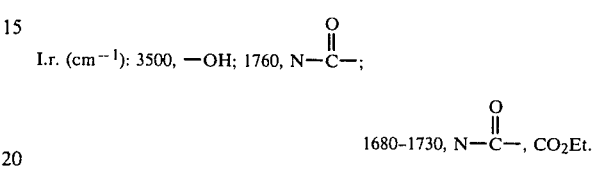

| Compound | R$_5$ | R$_1$ | R$_4$ |
|---|---|---|---|
| 19 | H | Et | C$_5$H$_{11}$ |
| 20 | Ph | Et | C$_5$H$_{11}$ |
| 21 | Me | Et | C$_5$H$_{11}$ |
| 22 | Et | Et | C$_5$H$_{11}$ |

Compound 19

Analysis: C$_{19}$H$_{35}$N$_3$O$_5$ requires C, 59.20; H, 9.15; N, 10.90% found: C, 59.50; H, 9.39; N, 10.63%

I.r. (cm$^{-1}$): 3500, —OH; 1760, —N—C(=O)—N;

1670-1730, —N—C(=O)—N, CO$_2$Et.

NMR (CCl$_4$) τ: 5.86 q, —CO$_2$CH$_2$CH$_3$; 6.1-6.7 brm, 2×N—CH$_2$, CH—OH, CH—OH; 7.71 brt, CH$_2$CO$_2$Et; 8.0-9.3 brm.

Compound 20

Analysis: C$_{25}$H$_{39}$N$_3$O$_5$ requires C, 65.05; N, 9.10; H, 8.52% Found: C, 65.13; N, 9.21; H, 8.71%

I.r. (cm$^{-1}$): 3500, —OH; 1765, —N—C(=O)—N;

1680-1740, —N—C(=O)—N, CO$_2$Et

NMR (CCl$_4$) τ: 2.6 brm, C$_6$H$_5$; 5.90 q, —CO$_2$CH$_2$CH$_3$; 6.1–6.9 brm, (N—CH$_2$), CH—OH, CH—OH; 7.75 brt, CH$_2$CO$_2$Et, 8.0–9.3 brm.

Compound 22

R$_5$=Et, R$_1$=Et, R$_4$=C$_5$H$_{11}$
Analysis: C$_{21}$H$_{39}$N$_3$O$_5$ requires C, 60.99; H, 9.51; N, 10.16% Found: C, 61.18; H, 9.47; N, 10.16%

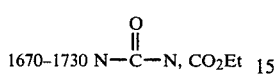

I.r. (cm$^{-1}$): 3500, —OH; 1760, —N—C—N;

1670–1730 N—C—N, CO$_2$Et

NMR (60 MHz, CDCl$_3$) τ: 5.91 brq, 3H, CH—OH, CO$_2$CH$_2$CH$_3$; 6.10–6.80 brm, 7H, (NCH$_2$)$_3$, CH—OH; 7.74 brt, 2H, CH$_2$CO$_2$Et; 8.0–9.3 brm.
Mass Spec. Meas. mass 413.2914, calc. mass 413.2889.

EXAMPLE 7

2-(3'-Hydroxy-n-octyl)-4-methyl-1,2,4-triazolidine-3,5-dione (Compound 23)

2-(3'-Oxo-n-octyl)-4-methyl-1,2,4-triazolidine-3,5-dione (0.5 g, 21 m mol) was dissolved in dry methanol (20 ml) and sodium borohydride (0.087 g, 2.3 m mol) was added portionwise. The reaction mixture was stirred overnight at room temperature and then the ethanol was removed by evaporation in vacuo. The residual gum was dissolved in water (20 ml) and acidified with 5 N aqueous hydrochloric acid, then extracted with ether (4×50 ml). The combined extracts were washed with brine (3×50 ml), dried (Na$_2$SO$_4$) and the ether removed by evaporation in vacuo to give a white residual solid, (0.36 g), m.p. 85°–88°, of 2-(3'-hydroxy-n-octyl)-4-methyl-1,2,4-triazolidine-3,5-dione (23).
Found, C, 54.77; H, 8.55% C$_{11}$H$_{21}$N$_3$O$_3$ requires, C, 54.30; H, 8.7%

I.R. (nujol, cm$^{-1}$): 3500, —OH; 1670–1760, N—C—.

NMR (60 MHz, CDCl$_3$) τ: 6.22 brq, 3H, N—CH$_2$, CH—OH; 6.90 s, 3H, —N—CH$_3$; 8.0–8.8 brm, 11H, (CH$_2$)$_5$, OH; 9.08 brt, 3H, CH$_3$.

EXAMPLE 8

1-(6'-Carboxy-n-hexyl)-2-(3''-hydroxy-n-octyl)-4-methyl-1,2,4-triazolidine-3,5-dione (Compound 24)

To a solution of 1-(6'-ethoxycarbonyl-n-hexyl)-2-(3''-hydroxy-n-octyl)-4-methyl-1,2,4-triazolidine-3,5-dione (0.43 g, 1.1 m mol) in dry ethanol (20 ml) was added anhydrous potassium carbonate (1.0 g) and the mixture boiled under reflux for 24 hours. The mixture was cooled, carefully acidified with ice-cold 5 N aqueous hydrochloric acid and extracted with ethyl acetate (4×100 ml). The combined extracts were washed with brine, dried (Na$_2$SO$_4$), filtered and ethyl acetate removed in vacuo to leave a gum (0.409 g). This gum was chromatographed on silica gel (Merck, Kieselgel 60) (20 g) using chloroform and chloroform-methanol mixtures (5% gradient) as eluant, to afford 1-(6'-carboxy-n-hexyl)-2-(3''-hydroxy-n-octyl)-4-methyl-1,2,4-triazolidine-3,5-dione (24) as a gum (200 mg).

Mass Spec. Meas. mass 371.2416, calc. mass 371.2421.

I.r. (cm$^{-1}$): 2400–3600, CO$_2$H, OH; 1640–1800, CO$_2$H, N—C—.

NMR (τ): 3.32 brs, 2H, CO$_2$H, OH; 6.4 brm, 5H, CH—OH, (N—CH$_2$)$_2$; (CDCl$_3$) 6.97s, 3H, N—CH$_3$; 7.70 brt, 2H, CH$_2$CO$_2$H.

EXAMPLE 9

1-(6'-Ethoxycarbonyl-n-hexyl)-2-(3''-hydroxy-3''-methyl-n-nonyl)-4-methyl-1,2,4-triazolidine-3,5-dione (Compound 25)

To a solution of 1-(6'-ethoxycarbonyl-n-hexyl)-(3''-oxo-n-nonyl)-4-methyl-1,2,4-triazolidine-3,5-dione (18) (0.82 g, 0.002 mol) in tetrahydrofuran (20 ml) cooled to −78° under a nitrogen atmosphere, methyl lithium (1.1. ml, 2.2 m mol) as a 2 M solution in ether was added dropwise. After complete addition the reaction mixture was stirred for a further 1 hr at −78°, allowed to warm to ca. −20° and then quenched with saturated ammonium chloride solution (20 ml). This mixture was extracted with ethyl acetate (4×50 ml); the combined extracts washed with brine (2×50 ml) dried (Na$_2$SO$_4$) and the solvent removed in vacuo to leave a gum (812 mg). This gum was chromatographed on silica gel (Merck, Kieselgel 60, 20 g) using chloroform as eluant to afford 1-(6'-ethoxycarbonyl-n-hexyl)-2-(3''-hydroxy-3''-methyl-n-nonyl)-4-methyl-1,2,4-triazolidine-3,5-dione (25) as a yellow gum (252 mg).

Mass spec. C$_{22}$H$_{41}$N$_3$O$_5$ requires M+ 427 found: M+ 427 (100%) Major 412 (M—Me, ca. 10%); 382 (M—OEt, ca 30%) 342 (M—C$_6$H$_{13}$, ca. 50%), 324 (M—H$_2$O, C$_6$H$_{13}$, ca. 20%); 322 (M—CH$_4$, C$_6$H$_{13}$, 20%), 296 (M—H$_2$O, C$_2$H$_4$, C$_6$H$_{13}$, 30%); 284 (M—C$_9$H$_{19}$O, 80%); 226 (M—C$_{12}$H$_{25}$O$_2$, 100%) 128 (M—C$_{18}$H$_{35}$O$_3$, 80%)

I.r. (cm$^{-1}$): 3500, —OH; 1760, —N—C—;

1670–1740, N—C—, CO$_2$Et

NMR (τ): 5.84q, 2H, CO$_2$CH$_2$CH$_3$; 4.05–4.55 m, 4H; (N—CH$_2$)$_2$; (CDCl$_3$) 6.92s, 3H, N—CH$_3$; 7.32 brs, 1H, —OH, 7.70 brt, 2H, CH$_2$CO$_2$Et.

The following Examples illustrate the preparation of the active compounds of the invention by the (XIII)→(XVII)→(XV)→(I) route, as illustrated in the flow diagram.

EXAMPLE 10

Preparation of hept-6-enoic acid

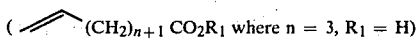
( (CH$_2$)$_{n+1}$ CO$_2$R$_1$ where n = 3, R$_1$ = H)

Ref: E. A. Brande, R. P. Linstead, and K. R. H. Wooldridge, JCS, 1956, 3074.

To a solution of sodium (19 g, 0.826 g atom) in ethanol (250 ml) at room temperature was added, dropwise, with stirring diethyl malonate (158 g, 1.0 mol) in ethanol (100 ml) and the mixture stirred for a further 1 hr at room temperature after complete addition.

To this mixture was added dropwise with stirring 5-bromopent-1-ene (100 g, 0.671 mol) in ethanol (50 ml) and after addition was complete the mixture was stirred for a further 12 hr at room temperature. This resultant mixture was acidified by the addition of acetic acid (15 ml) and the ethanol was removed in vacuo. The residue was mixed with ether (500 ml), filtered and the filtrate was washed with saturated sodium chloride solution until neutral. The organic phase was then dried ($Na_2SO_4$) filtered and the ether removed in vacuo. The resultant liquid was distilled to afford diethyl-pent-4-enyl-malonate b.p. 131°–6°/14 mm (80 g) (ref. b.p. 134°/14 mm).

The diethyl-pent-4-enylmalonate (80 g, 0.351 mol) was added to a solution of potassium hydroxide (120 g, 2.143 mol) in water (75 ml) containing ethanol (15 ml) and the resultant mixture stirred for 12 hr at room temperature. This mixture was then acidified with 5 N sulphuric acid (ca. 250 ml) and concentrated sulphuric acid (ca. 25 ml) and the resultant mixture extracted with ether (3×200 ml). The combined extracts were washed with water (2×200 ml) and saturated sodium chloride solution (2×200 ml). The organic phase was dried ($Na_2SO_4$), filtered and the ether removed from the filtrate in vacuo. The residual oil was decarboxylated at a bath temperature of 160° and pressure 20 mm Hg and the hept-6-enoic acid collected at 120°/20 mm. (38.2 g) (ref. b.p. 74°/0.5 mm).

EXAMPLE 11

(a) Preparation of 1-(6'-methoxycarbonyl-n-hexyl)-4-methyl-1,2,4-triazoli-dine-3,5-dione (26)

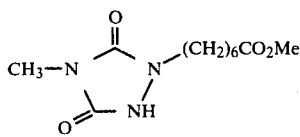
(2)

Dinitrogen tetroxide was bubbled through a suspension of 4-methyl-1,2,4-triazolidine-3,5-dione (23.0 g, 0.2 mol) in dichloromethane (250 ml) cooled to 0° C., until a clear, homogenous deep red solution was obtained. This solution was then dried ($Na_2SO_4$), filtered, and the filtrate evaporated at room temperature in vacuo to give 4-methyl-1,2,4-triazolidine-3,5-dione (m.p. 105° decomp). To the 4-methyl-1,2,4-triazolidine-3,5-dione (23.0 g, 0.2 mol) dissolved in benzene (200 ml) was added dropwise hept-6-enoic acid (23.0 g, 0.18 mol) in benzene (100 ml) and the resultant solution boiled under reflux in an atmosphere of nitrogen, until a pale yellow solution had been obtained (in 1 hr). The resultant solution was evaporated in vacuo and the residue dissolved in a 10% solution of acetyl chloride in methanol (300 ml). This solution was boiled at reflux for 5 hr, stirred at room temperature overnight and then evaporated in vacuo. The residue (44 g) was chromatographed on silica gel (Merck Kieselgel 60, 900 g) using chloroform; methanol as eluant (0–5% methanol), to afford 1-(6'-methoxycarbonyl-n-hex-2-enyl)-4-methyl-1,2,4-triazolidine-3,5,-dione (19.1 g) m.p. 55–7.

found: C, 51.55; H, 6.56; N 16.59%
$C_{11}H_{17}N_3O_4$ requires C, 51.76; H, 6.71; N 16.46%
NMR ($CDCl_3$) τ: 0.8–1.2 brs, 1H, N—H; 4.37 m, 2H, CH=CH; 5.97 brd, 2H, N—$CH_2$—; 6.40s, 3H, —$CO_2CH_3$; 7.00, S, 3H, N—$CH_3$; 7.5–8.8 brm, 6H, —($CH_2$—)$_3$.

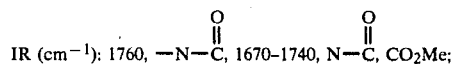

Mass Spec. Meas. mass 255.1243 calc. mass 255.1219.

(b) Preparation of 1-(6'-methoxycarbonyl-n-hexyl)-4-methyl-1,2,4-triazoli-dine-3,5-dione The 1-(6'-methoxycarbonyl-n-hex-2-enyl)-4-methyl-1,2,4-triazolidine-3,5-dione (12.4 g, 0.0486 mol) was dissolved in dimethoxyethane (200 ml) and 10% palladium on charcoal (3 g) was added and the resultant mixture was allowed to take up hydrogen (ca. 1100 mls). After the reaction was complete the resultant mixture was filtered through a kieselguhr bed and the filtrate evaporated in vacuo to afford 1-(6'-methoxycarbonyl-n-hexyl)-4-methyl-1,2,4-triazolidine-3,5-dione (12.3 g). m.p. 80°–1°.

found: C, 51.12; H, 7.71; N 16.38% $C_{11}H_{19}N_3O_4$ requires C, 51.35; H, 7.44; N, 16.33%.

NMR ($CDCl_3$) τ: 6.39s, 6.48 m, 5H, —$CO_2CH_3$; —N—$CH_2$—; 6.97s, 3H, N—$CH_3$; 7.73 m, 2H, —$CH_2CO_2Me$; 9.07–9.78 brm, —($CH_2$)$_4$, 8H.

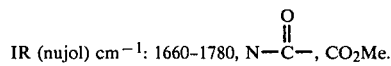

Mass Spec. Meas. mass 257.1377 calc. mass 257.1375.

EXAMPLE 12

Preparation of 1-(p-toluenesulphonyl)-3-cyclohexylbutan-3-ol

To a slurry of zinc (33 g, 0.5 mol) in benzene (50 ml) containing a small crystal of iodine, boiled at reflux, was added carefully 40 ml of a mixture of cyclohexylmethyl ketone (37 g, 0.294 mol), ethyl bromoacetate (84 g, 0.5 mol) and benzene (50 ml). After initiation of the reaction, the rest of the mixture was added at such a rate that reflux was maintained. After complete addition of the ketone mixture the resultant reaction mixture was boiled at reflux for a further 1 hr. The mixture was then cooled and poured into ice-cold 20% sulphuric acid (200 ml) and extracted with ether (4×200 ml). The combined extracts were washed with water (2×250 ml), saturated sodium hydrogen carbonate solution (2×250 ml) and saturated sodium chloride solution until neutral. The extract was then dried ($Na_2SO_4$), filtered and the filtrate evaporated in vacuo to remove ether to give an oil (97 g). This residual oil was then distilled to afford ethyl-3-cyclohexyl-3-hydroxy-butyrate, (36 g) b.p. 90°–94°/0.05 mm.

To a slurry of lithium aluminium hydride (6.39 g, 0.168 mol) in ether (250 ml), in an atmosphere of nitrogen and cooled in an ice-bath was added dropwise ethyl-3-cyclohexyl-3-hydroxybutyrate (36 g, 0.168 mol) in ether (100 ml). After complete addition of the ester the resultant mixture was boiled at reflux for 1 hr, then cooled in an ice-bath. Excess lithium aluminium hydride was destroyed by successive dropwise addition of water (7 ml), 10% sodium hydroxide solution (7 ml) and water (21 ml). The reaction mixture was filtered, the filter cake washed with ether (2×100 ml) and the filtrate washed with saturated sodium chloride solution (1×250 ml) and then dried (Na₂SO₄). This mixture was filtered and the filtrate evaporated in vacuo to remove ether to give 3-cyclohexylbutane-1,3-diol (25 g) as an oil.

NMR (CDCl₃)₂ τ: 5.51, 1H, —OH; 6.26 brm, 3H, —OH, C$\underline{H}_2$—OH; 8.0-9.5 brm, 8.92s, 16H, —(CH₂)₆, —C$\underline{H}$—, CH₃

IR (cm⁻¹) 3500, —OH.

The 3-cyclohexylbutan-1,3-diol (25 g, 0.145 mol) was dissolved in pyridine (130 ml) and cooled to 0° C. with stirring. Toluene sulphonyl chloride (29 g, 0.152 mol) was added portionwise and the resultant reaction mixture stirred for 45 minutes at 0°. The reaction mixture was then stored in a refrigerator for 15 hr and then poured into iced-water (200 ml). The reaction mixture was extracted with ether (3×200 ml) and the combined extracts washed with 10% HCL (2×200 ml), saturated sodium chloride solution (3×200 ml) and then dried (Na₂SO₄). This mixture was filtered and the filtrate evaporated in vacuo at room temperature to remove ether to leave a gum (45 g). This gum was mixed with petrol (bp 60°-80°, 200 ml) gradually cooled to −78° with stirring, and the petrol decanted. Residual petrol was removed by evaporation in vacuo at room temperature to leave 1-(p-toluene sulphonyl)-3-cyclohexybutan-3-ol (40 g) as a gum.

found: C, 62.36; H, 7.99. S, 9.40% C₁₇H₂₆SO₄ requires C, 62.56; H, 8.03; S, 9.80%

IR (cm⁻¹): 3600, OH; 1190, 1180, 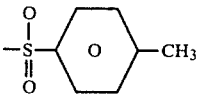

The ethyl hydroxyesters and corresponding tosylates given in Table 1. were prepared in a similar manner.

TABLE 5

Characterising data for ethyl-3-alkyl(aryl)-3-hydroxy alkanoates (4) and 1-(p-toluene sulphonyl)-3-alkyl(aryl) alkan-3-ols(3).

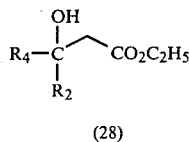
(28)

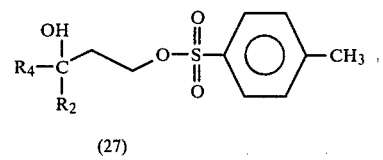
(27)

| ESTER (28) | | | TOSYLATE (27) | | | | |
|---|---|---|---|---|---|---|---|
| | | | ANALYSIS, found (calcd) | | | I.R. cm⁻¹ | |
| R₄ | R₂ | b.p.°/mmHg | C | H | S | —OH | —OTS |
| C₆H₁₃— | CH₃— | 84.88/0.1 | 62.39(62.18) | 8.89(8.59) | 9.27(9.76) | 3550 | 1180 br |
| ⌬— | CH₃— | 92-6/0.1 | 63.64(63.74) | 6.37(6.29) | 9.78(9.99) | 3580 | 1185,1195 |
| ⌬—CH₂— | CH₃ | 102-106/0.5 | 64.66(64.66) | 7.11(6.63) | 8.94(9.57) | 3600 | 1190 br |
| C₄H₉CH(CH₃)— | CH₃— | 84-86/0.1 | 62.05(62.18) | 9.04(8.59) | 9.31(9.76) | 3600 | 1180,1190 |
| ⌬— | CH₃— | 90-4/0.05 | 62.36(62.56) | 7.99(8.03) | 9.40(9.80) | 3600 | 1185,1195 |
| Me—⌬— | CH₃— | 116/118/0.07 | 64.95(64.66) | 6.65(6.63) | — | 3550 | 1185,1195 |
| △— | CH₃— | 50-54/0.05 | 61.55(59.14) | 7.61(7.09) | 10.95(11.25) | 3550 | 1185,1190 |
| C₉H₁₉— | CH₃ | 132/134/0.05 | 64.82(64.8) | 9.57(9.25) | 8.6(8.64) | 3550 | 1180,1190 |
| Me—⌬— | CH₃—² | | 67.26(67.32) | 8.19(8.22)¹ | — | 3400 | 1180,1190 |
| ⌬⌬— | CH₃—³ | | | | | 3550 | 1180,1190 |
| F—⌬— | CH₃— | 102-104/0.05 | — | — | — | 3600 | 1185,1195 |

TABLE 5-continued

Characterising data for ethyl-3-alkyl(aryl)-3-hydroxy alkanoates (4) and 1-(p-toluene sulphonyl)-3-alkyl(aryl) alkan-3-ols(3).

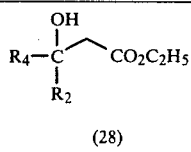
(28)

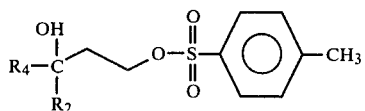
(27)

| ESTER (28) | | | TOSYLATE (27) | | | | |
|---|---|---|---|---|---|---|---|
| | | | ANALYSIS, found (calcd) | | | I.R. cm$^{-1}$ | |
| $R_4$ | $R_2$ | b.p.°/mmHg | C | H | S | —OH | —OTS |
| PhCH$_2$O—⟨O⟩— | CH$_3$— | GUM[4] | — | — | — | 3550 | 1180 br |

[1] Diol analysed due to decomposition of tosylate
[2] not purified due to decomposition
[3] Diol purified by chromatography
[4] Purified by chromatography

EXAMPLE 13

(a) Preparation of 1-(6'-methoxycarbonyl-n-hexyl)-2-(3''-hydroxy-3''-methyl-n-nonyl)-4-methyl-1,2,4-triazolidine-3,5-dione. (29) (by procedure 1)

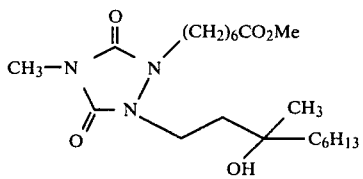

To a solution of 1-(6'-methoxycarbonyl-n-hexyl)-4-methyl-1,2,4-triazolidine-3,5-dione(26) (6.428 g, 0.025 mol) in hexamethylphosphoramide (40 ml) was added sodium carbonate (3.18 g, 0.03 mol), sodium iodide (1 g, 0.007 mol) and 1-(p-toluenesulphonyl)-3-methylnonan-3-ol (8.204 g, 0.025 mol) in hexamethylphosphoramide (30 ml) and the resultant mixture stirred at room temperature for 70 hr. The reaction mixture was then poured into water (200 ml), acidified with 10% hydrochloric acid and extracted with ethyl acetate (3×200 ml). The combined extracts were washed with water (3×250 ml) saturated sodium chloride solution (3×250 ml) and then dried (Na$_2$SO$_4$). This mixture was filtered and the filtrate evaporated in vacuo to remove ethyl acetate to leave a gum (9.54 g). This gum was chromatographed on silica gel (Merck Kieselgel 60) (500 g) using chloroform:methanol as eluant (0–2% methanol) to afford 1-(6'-methoxy-carbonyl-n-hexyl)-2-(3''-hydroxy-3''-methyl-n-nonyl)-4-methyl-1,2-4-triazolidine-3,5-dione(29) (2.95 g) as a gum.

found: C, 60.51; H 9.72; N, 10.05% C$_{21}$H$_{39}$N$_3$O$_5$ requires C, 60.99; H, 9.51; N 10.16% NMR (CDCl$_3$) τ: 6.35s, 6.36 m, 7H, —CO$_2$CH$_3$, (N—CH$_2$)$_2$; 6.96s, 3H, —N—CH$_3$; 7.46-7.84, 3H, CH$_2$—CO$_2$Me; —OH 8.01-8.90 m, 8.81s, 9.11 m, 26H, ᛋ(CH$_2$)$_{10}$, CH$_3$—C—OH, —CH$_2$CH$_3$ IR (cm$^{-1}$): 3500, —OH; 1770 —N—C(=O)—; 1680-1740 —N—C(=O)—, CO$_2$Me.

Mass Spec: found M+ 413.2829. Calc. M+ 413.2769.

(b) Preparation of 1-(6'-methoxycarbonyl-n-hexyl)-2-(3''-hydroxy-3''-cyclopropyl-n-butyl)-4-methyl-1,2,4-triazolidine-3,5,dione (35) (by procedure 2)

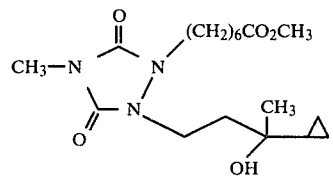
(6)

To a solution of 1-(6'-methoxycarbonyl-n-hexyl)-4-methyl-1,2,4-triazolidine-3,5-dione (2.0 g, 0.0078 mol) in N,N-dimethylformamide (20 ml) stirred at room temperature was added portionwise sodium hydride (0.26 g, 0.0087 mol) as an 80% dispersion in mineral oil and the mixture stirred for 0.5 hr at room temperature. To this solution was added anhydrous lithium iodide (2.3 g, 0.017 mol) and the resultant mixture stirred for a further 0.5 hr at room temperature. To this resultant solution was added 1-(p-toluene sulphonyl)-3-cyclopropylbutan-3-ol (2.22 g, 0.0078 mol) in N,N-dimethylformamide (20 ml) and the reaction mixture was stirred for 24 hr at 50°. The reaction mixture was then poured into water (200 ml), acidified with 10% hydrochloric acid and extracted with ethyl acetate (3×250 ml). The combined extracts were washed with water (3×250 ml) and saturated sodium chloride solution (2×250 ml) and then dried (Na$_2$SO$_4$), filtered and the filtrate evaporated in vacuo to remove ethyl acetate to afford a gum (3.51 g). This gum was chromatographed on silica gel (Merck Kieselgel 60, 200 g) using chloroform:methanol as eluant (methanol 0–2%) to afford 1-(6'-methoxycarbonyl-n-hexyl)-2-(3''-hydroxy-3''-cyclopropyl-n-butyl)-4-methyl-1,2,4-triazolidine-3,5-dione (35) as a gum (558 mg).

The 1,2,4-trisubstituted-1,2,4-triazolidine-3,5-diones given in Table 6 were prepared in a similar manner using either procedure (1) or (2); except (i) the acids (wherein $R_1$=H) which were prepared by the procedure illustrated in Example 14, and (ii) the unsaturated olefinic analogues (wherein Y is CH=CH) which were prepared by the procedure illustrated in Example 15.

The characterising data for these compounds is given in a separate section.

TABLE 6

1,2,4-trisubstituted-1,2,4-triazolidine-3,5-diones

| No: | $R_1$ | $R_2$ | $R_3$ | $R_4$ | $R_5$ | Y | n | Procedure |
|---|---|---|---|---|---|---|---|---|
| 29 | $CH_3$ | $CH_3$ | OH | $C_6H_{13}$ | $CH_3$ | $CH_2-CH_2$ | 3 | 1 |
| 30 | $CH_3$ | $CH_3$ | OH | $C_6H_5$ | $CH_3$ | $CH_2-CH_2$ | 3 | 1 |
| 31 | $CH_3$ | $CH_3$ | OH | $C_6H_5CH_2$ | $CH_3$ | $CH_2-CH_2$ | 3 | 1 |
| 32 | $CH_3$ | $CH_3$ | OH | $C_4H_9CH(CH_3)-$ | $CH_3$ | $CH_2-CH_2$ | 3 | 1 |
| 33 | $CH_3$ | $CH_3$ | OH | cyclohexyl | $CH_3$ | $CH_2-CH_2$ | 3 | 1 |
| 34 | $CH_3$ | $CH_3$ | OH | 4-Me-C$_6$H$_4$ | $CH_3$ | $CH_2-CH_2$ | 3 | 1 |
| 35 | $CH_3$ | $CH_3$ | OH | cyclopropyl | $CH_3$ | $CH_2-CH_2$ | 3 | 2 |
| 36 | $CH_3$ | $CH_3$ | OH | $C_9H_{19}$ | $CH_3$ | $CH_2-CH_2$ | 3 | 1 |
| 37 | $CH_3$ | $CH_3$ | OH | 4-MeO-C$_6$H$_4$ | $CH_3$ | $CH_2-CH_2$ | 3 | 1 |
| 38 | $CH_3$ | $CH_3$ | OH | naphthyl | $CH_3$ | CH=CH | 3 | 1 |
| 39 | $CH_3$ | $CH_3$ | OH | 4-F-C$_6$H$_4$ | $CH_3$ | $CH_2-CH_2$ | 3 | 1 |
| 40 | $CH_3$ | $CH_3$ | OH | $CH_3$ | $CH_3$ | $CH_2-CH_2$ | 3 | 1 |
| 41 | H | $CH_3$ | OH | $C_6H_{13}$ | $CH_3$ | $CH_2-CH_2$ | 3 | — |
| 42 | H | $CH_3$ | OH | $C_6H_5$ | $CH_3$ | $CH_2-CH_2$ | 3 | — |
| 43 | $CH_3$ | $CH_3$ | OH | $C_6H_{13}$ | $CH_3$ | CH=CH | 3 | 1 |
| 44 | H | $CH_3$ | OH | $C_6H_{13}$ | $CH_3$ | CH=CH | 3 | — |
| 45 | $CH_3$ | $CH_3$ | OH | $C_6H_{13}$ | cyclohexyl | $CH_2-CH_2$ | 3 | 1 |
| 46 | $CH_3$ | $CH_3$ | OH | $C_6H_{13}$ | Ph | $CH_2-CH_2$ | 3 | 1 |
| 47 | $CH_3$ | $CH_3$ | OH | $C_6H_{13}$ | 3-Me-C$_6$H$_4$ | $CH_2-CH_2$ | 3 | 1 |
| 48 | H | $CH_3$ | OH | $C_6H_{13}$ | 3-Me-C$_6$H$_4$ | $CH_2-CH_2$ | 3 | — |
| 49 | $CH_3$ | $CH_3$ | OH | $C_6H_{13}$ | PhCH$_2$ | CH=CH | 3 | 1 |

EXAMPLE 14

Preparation of 1-(6'-carboxy-n-hexyl)-2-(3''-hydroxy-3''-methyl-n-nonyl)-4-methyl-1,2,4-triazolidine 3,5-dione (41)

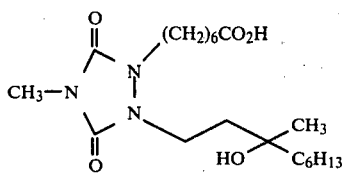

To a solution of 1-(6'-methoxycarbonyl-n-hexyl)-2(3''-hydroxy-3''-methyl-n-nonyl)-4-methyl-1,2,4-triazolidine-3,5-dione (5) (2.423 g, 0.006 mol) in methanol (100 ml) was added a 10% aqueous solution of sodium carbonate (30 ml) and the mixture boiled at reflux for 18 hr. The reaction mixture was cooled and evaporated in vacuo. The residue was dissolved in water (100 ml) and extracted with ether (3×100 ml). The aqueous phase was then acidified with 10% hydrochloric acid and reextracted with ethyl acetate (3×200 ml). The combined extracts were washed with saturated sodium chloride solution (2×200 ml) dried ($Na_2SO_4$), filtered and the filtrate evaporated in vacuo to remove ethyl acetate to afford 1-(6'-carboxy-n-hexyl)-2-(3''-hydroxy-3''-methyl-n-nonyl)-4-methyl-1,2,4-triazolidine-3,5-dione (41) as a gum (2.404 g).

EXAMPLE 15

Preparation of 1-(6'-methoxycarbonyl-n-hex-2-enyl)-2-(3''-hydroxy-3''-methyl-n-nonyl)-4-methyl-1,2,4-triazolidine-3,5-dione (43) was carried out as in Procedure (1) of Example 13 using 1-(6'-methoxycarbonyl-n-hex-2-enyl)-4-methyl-1,2,4-triazolidine-3,5-dione instead of 1-(6'-methoxycarbonyl-n-hexyl)-4-methyl-1,2,4-triazolidine-3,5-dione.

CHARACTERISING DATA FOR COMPOUNDS GIVEN IN TABLE 2

Compound 30

NMR ($CDCl_3$) $\tau$: 2.45–2.82 brm, 5H, —$C_6H_5$; 6.295, 6.30–6.77 brm, 7H, —$CO_2CH_3$, —(N—$CH_2$)$_2$; 7.015, N—$CH_3$, 3H; 7.25s, 1H, —$OH$ (exchanged with $D_2O$); 7.51–8.09 m, 8.41 s, 8.69 brs, 15H.

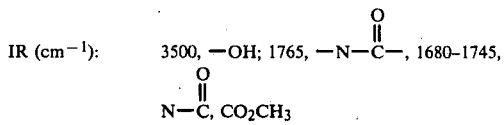

Mass Spec. found M+ 405.2258 Calc. $C_{21}H_{31}N_3O_5$: 405.2252

Compound 31

Analysis: found: C, 61.51; H, 8.23; N, 9.96% $C_{22}H_{33}N_3O_5$ requires C, 62.99; H, 7.93; N, 10.02%

NMR($CDCl_3$) $\tau$: 2.75 s, 5H, —$C_6H_5$; 6.32m, 6.36s, 7H, (N—$CH_2$)$_2$, $CO_2CH_3$; 6.96s, 3H, —N—$CH_3$; 7.23s, 2H, $C_6H_5CH_2$—; 7.54s, 7.70t, 3H, —OH, $CH_2CO_2Me$; 8.09–9.08m, 8.81s, —($CH_2$)$_5$—, $CH_3$ C—OH, 13H.

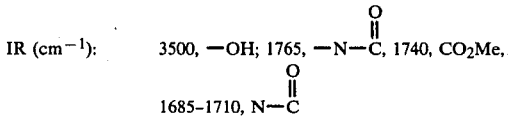

Mass Spec: found M+ 419.2429 Calc. $C_{22}H_{33}N_3O_5$: 419.2420

Compound 32

NMR ($CDCl_3$) $\tau$: 6.32m, 6.34 s, 7H, (n—$CH_2$)$_2$, $CO_2CH_3$; 6.95s, N—$CH_3$, 3H; 7.75m, 3H, —$OH$, $CH_2CO_2Me$; 8.1–9.4m, 8.88s, 26H, —($CH_2$)$_8$—; $CH$—$CH_3$; $CH_3$—C—OH, $CH_3$—$CH_2$.

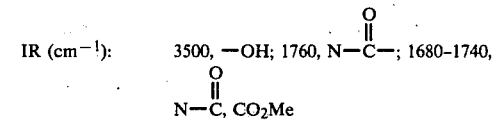

Mass Spec. found M+ Calc. $C_{21}H_{39}N_3O_5$ 413.2959 413.2889.

Compound 33

NMR ($CDCl_3$) $\tau$: 6.31s, 6.37m, 7H, $CO_2Me$, —(N—$CH_2$)$_2$;— 6.93s, 3H, N—$CH_3$; 7.67m, 3H, —$OH$, $CH_2CO_2Me$ 7.98–9.30m, 8.86s, 24H, —($CH_2$)$_{10}$, $CH$—$CH_2$, $CH_3$—C—OH.

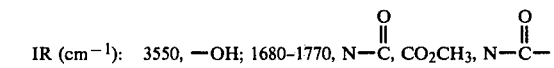

Mass Spec. found M+ 411.2690 Calc. M+ $C_{21}H_{37}N_3O_5$ 411.2647

Compound 34

Analysis found; C 63.34; H, 7.71; N 10.08% $C_{22}H_{33}N_3O_5$ requires C, 62.99; H, 7.93; N, 10.02%

NMR ($CDCl_3$) $\tau$: 2.60–2.93m, 4H, $C_6H_4$; 6.33 s, 3H, —$CO_2CH_3$; 6.58 brt, 4H, (—$NCH_2$)$_2$; 7.04s, 3H, —N—$CH_3$; 7.66s, 7.50–8.68 brm, 8.45s, 19H, $C_6H_5$—$CH_3$, —OH; (—$CH_2$—)$_6$, $CH_3$—

IR ($cm^{-1}$): 3550, —OH; 1680–1770, N—C, $CO_2CH_3$, N—C—
         O                                O

Mass Spec. found M+ 419.2446 Calcd. M+ $C_{22}H_{33}N_3O_5$ 419.2420

Compound 35

NMR ($CDCl_3$) $\tau$: 6.00–6.77 brm, 6.35s, 7H, (N—$CH_2$)$_2$, —$CO_2CH_3$; 6.96s, 3H, N—$CH_3$; 7.69 brt, 3H, —OH, $CH_2CO_2Me$; 8.0–9.37 brm, 8.82s, 14H, ($CH_2$)$_5$, $CH_3$, $CH$>; 9.4–9.8 brm, 4H, ($CH_2$)$_2$.

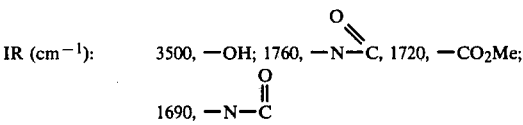

Mass Spec: found Mass 369.2246 Calc. mass 369.2247.

Compound 36

Analysis: Found: C, 62.90; H, 9.74; N, 9.26%. $C_{24}H_{45}N_3O_5$ requires: C, 63.27; H, 9.95; N, 9.22%.
NMR (60 MHz, CDCl$_3$) τ: 6.0–6.45 m, 6.35 s, (N—C$\underline{H}_2$)$_2$, —CO$_2$C$\underline{H}_3$; 6.95 s, 3H, N—C$\underline{H}_3$; 7.5–7.85 m, 3H, C$\underline{H}_2$CO$_2$CH$_3$, O$\underline{H}$; 8.0–8.8 brm, 29H, 9.1 brt, 3H, —C$\underline{H}_3$.

I.r. (cm$^{-1}$):  3550, —OH;

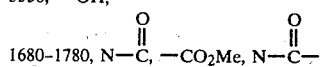
1680–1780, N—C, —CO$_2$Me, N—C—

Compound 37

Analysis: Found: C, 60.49; H, 7.92; N, 9.52%. $C_{22}H_{33}N_3O_6$ requires: C, 60.67; H, 7.64; N, 9.65%.
NMR (60 MHz, CDCl$_3$) τ: 2.6–3.25 m, 4H, —C$_6$$\underline{H}_4$; 6.2 s, 3H, —OC$\underline{H}_3$; 6.35 s, 3H, CO$_2$C$\underline{H}_3$; 6.4–6.8 m, 4H, (N—C$\underline{H}_2$)$_2$; 7.05 s, 3H, N—CH$_3$; 7.45 brs, 1H, —O$\underline{H}$; 7.6–8.2 brm, C$\underline{H}_2$—C(OH), C$\underline{H}_2$CO$_2$Me; 8.2–8.9 brm, 8.46 s, 11H, (C$\underline{H}_2$)$_4$, CH$_3$—C—OH.

I.r. (cm$^{-1}$):  3500, —OH;

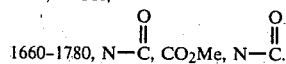
1660–1780, N—C, CO$_2$Me, N—C.

Compound 38

NMR (60 MHz, CDCl$_3$) τ: 2.0–2.62 m, 7H, —C$_{10}$$\underline{H}_7$; 4.62 brq, 2H, —C$\underline{H}$=C$\underline{H}$; 5.93–6.13 brm, 2H, —C$\underline{H}_2$—CH=CH; 6.34 s, 6.23–6.60 brm, 6H, CO$_2$C$\underline{H}_3$, N—C$\underline{H}_2$, —O$\underline{H}$; 7.18 s, 3H, —NC$\underline{H}_3$; 7.62–8.50 brm, 8.34 s, 11H.

I.r. (cm$^{-1}$): 3500, —OH, 1660–1780, N—C, CO$_2$CH$_3$, N—C.

Compound 39

NMR (CDCl$_3$, 60 MHz) τ: 2.47–3.15 m, 4H, C$_6$$\underline{H}_4$; 6.36 s, 6.36–6.74 brm, 6.90 brs, 7.04 s, 11H, —CO$_2$CH$_3$, —(NCH$_2$)$_2$, —O$\underline{H}$, —N—C$\underline{H}_3$; 7.55–8.15 brm, 8.30–8.90 brm, 8.50 s, 15H, (CH$_2$)$_6$, —CH$_3$.

I.r. (cm$^{-1}$):  3500, —OH; 1660–1780, N—C—, CO$_2$Me,
N—C—; 1602, aromatic.

Mass Spec. Meas. mass, 423.2198; calc. mass, M$^+$, 423.2170.

Compound 40

NMR (CDCl$_3$, 60 MHz) τ: 6.12–6.58 brm, 6.30 s, 7H, (N—CH$_2$)$_2$, —CO$_2$CH$_3$; 6.91 s, 3H, —N—CH$_3$; 7.50–8.90 brm, 8.70 s, 19H.

I.r. (cm$^{-1}$):  3500, —OH; 1760, N—C;
1680–1740, N—C, CO$_2$Me.

Mass Spec. Meas. mass, 343.2097; calc. mass, M$^+$, 343.2107.

Compound 41

Analysis: Found: C, 59.61; H, 9.57; N, 10.38%. $C_{20}H_{37}O_5N_3$ requires: C, 60.13; H, 9.33; N, 10.52%.
NMR (60 MHz, DMSO) τ: 6.2–6.7 brm, 4H, (N—C$\underline{H}_2$)$_2$; 7.09 s, 3H, N—C$\underline{H}_3$; 7.81 brt, 2H, C$\underline{H}_2$CO$_2$H; 8.2–9.4 brm, 9.93 s, 9.12 brt, 26H, –(CH$_2$)$_{10}$, CH$_3$, CH$_2$CH$_3$.

I.r. (cm$^{-1}$):  2500–3500, OH; 1770, N—C—;
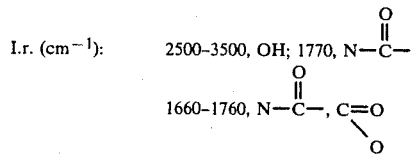
1660–1760, N—C—, C=O / \O Mass Spec. Meas. mass 399.2688; calc. mass 399.2734.

Compound 42

Analysis: Found: C, 60.93; H, 7.62; N, 10.72%. $C_{20}H_{29}N_3O_5$ requires: C, 61.36; H, 7.47; N, 10.73%.
NMR (60 MHz, CDCl$_3$) τ: 2.5–2.85 brm, 5H, —C$_6$$\underline{H}_5$; 3.72 brs, 2H, CO$_2$$\underline{H}$, O$\underline{H}$; 6.15–6.85 brm, 4H, (N—C$\underline{H}_2$)$_2$; 7.05 s, 3H, N—C$\underline{H}_3$; 7.50–8.15 brm, 8.44 s, 8.72 brs, 15H.

I.r. (cm$^{-1}$):  2500–3500, —OH; 1660–1780,
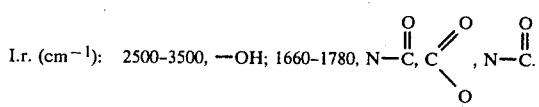

Mass Spec. Meas. mass M$^+$ 391.2116; calc. mass 391.2107.

Compound 43

NMR (60 MHz, CDCl$_3$) τ: 3.92–4.92 m, 2H, C$\underline{H}$=C$\underline{H}$; 5.84 d, 2H, J=5 Hz, C$\underline{H}_2$—CH=CH—; 6.26 m, 6.30 s, 5H, —N—C$\underline{H}_2$, —CO$_2$C$\underline{H}_3$; 6.91 s, 3H, N—C$\underline{H}_3$; 7.55–8.82 m, 8.76 s, 9.06 m, 25H.

I.r. (cm$^{-1}$):  3600, OH; 1770, N—C;
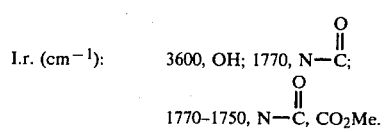
1770–1750, N—C, CO$_2$Me.

Mass Spec. Meas. mass (for M$^+$ —C$_6$H$_{13}$), 326.1700; Calc. mass, 326.1716. No M$^+$.

Compound 44

NMR (CDCl$_3$, 60 MHz) τ: 4.20–4.60 brm, 2H, C$\underline{H}$=C$\underline{H}$; 4.90 brs, 2H, —CO$_2$$\underline{H}$, —O$\underline{H}$; 5.85 brd, 2H, N—C$\underline{H}_2$; 6.10–6.45 m, 2H, N—C$\underline{H}_2$; 6.91 s, 3H, N—C$\underline{H}_3$; 7.50–9.20 brm, 8.77 s, 9.08 brt.

I.r. (cm$^{-1}$):  2600–3500, —OH; 1760, N—C;
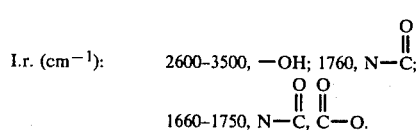
1660–1750, N—C, C—O.

Mass Spec. Meas. mass, 397.2573; calc. mass, 397.2577.

Compound 45

NMR (CDCl$_3$, 60 MHz) τ: 5.5–5.7 brt, 1H, CH—N; 6.1–6.65 brt, 4H, (—NCH$_2$)$_2$; 6.35 s, 3H, CO$_2$CH$_3$; 7.55–7.85 m, 3H, CH$_2$CO$_2$CH$_3$, OH; 7.85–9.0 m, 33H, —(CH$_2$)$_4$, C$_5$H$_{10}$—CH—N, (CH$_2$)$_6$, CH$_3$; 9.1 m, 3H, CH$_2$CH$_3$.

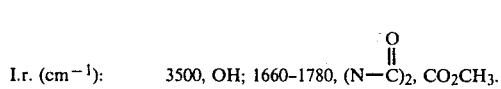

I.r. (cm$^{-1}$): 3500, OH; 1660–1780, (N—C)$_2$, CO$_2$CH$_3$.

Mass spec. Meas. mass, M$^+$, 481.3539; calc. mass, M$^+$, 481.3516.

Compound 46

NMR (CDCl$_3$, 60 MHz) τ: 2.55–2.65 m, 5H, C$_6$H$_5$; 6.05–6.5 brt, 4H, (—NCH$_2$)$_2$; 6.33 s, 3H, CO$_2$CH$_3$; 7.55–7.85 m, 3H, CH$_2$CO$_2$CH$_3$, OH; 7.85–9.0 m, 23H, —(CH$_2$)$_4$—,

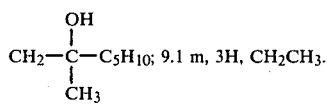

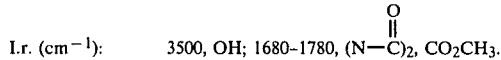

I.r. (cm$^{-1}$): 3500, OH; 1680–1780, (N—C)$_2$, CO$_2$CH$_3$.

Mass spec. Meas. mass, M$^+$, 475.3027; calc. mass, M$^+$, 475.3008.

Compound 47

Analysis: Found: C, 65.96; H, 8.56; N, 8.26%. C$_{27}$H$_{43}$N$_3$O$_5$ requires: C, 66.23; H, 8.85; N, 8.58%. NMR (CDCl$_3$, 60 MHz) τ: 2.6–2.9 m, 4H, C$_6$H$_4$; 6.0–6.45 brt, 4H, —(NCH$_2$)$_2$; 6.35 s, 3H, CO$_2$CH$_3$; 7.5–7.8 m, 3H, CH$_2$CO$_2$CH$_3$, OH; 7.6 s, 3H, C$_6$H$_4$CH$_3$; 7.8–9.0 m, 23H, —(CH$_2$)$_4$—,

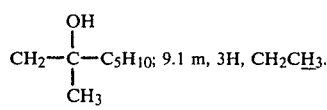

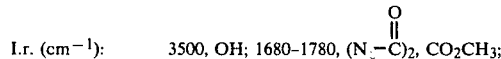

I.r. (cm$^{-1}$): 3500, OH; 1680–1780, (N—C)$_2$, CO$_2$CH$_3$;

Mass Spec. Meas. mass, M$^+$, 489.3237; calc. mass, M$^+$, 489.3203.

Compound 48

NMR (CDCl$_3$, 60 MHz) τ: 2.6–2.9 m, 4H, C$_6$H$_4$; 4.1 s, 1H, CO$_2$H; 6.05–6.4 brt, 4H, —(NCH$_2$)$_2$; 7.65 s, 3H, C$_6$H$_4$CH$_3$; 7.65–7.8, 3H, CH$_2$CO$_2$CH$_3$, OH; 7.8–9.0 m, 23H, —(CH$_2$)$_4$,

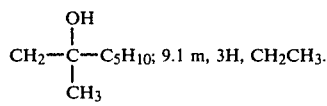

I.r. (cm$^{-1}$): 3400, OH, CO$_2$H; 1680–1780, (N—C)$_2$, CO$_2$H.

Mass Spec. Meas. mass, M$^+$, 475.3046; calc. mass, M$^+$, 475.3046.

Compound 49

NMR (CDCl$_3$, 60 MHz) τ: 2.68 brs, 5H, —C$_6$H$_5$; 4.02–5.04 brm, 2H, CH=CH; 5.34 brs, 2H, CH$_2$Ph; 5.62–6.05 brm, 2H, N—CH$_2$—; 6.18–6.44 brm, 6.35 s, 5H, N—CH$_2$, —CO$_2$CH$_3$; 7.50–9.30 brm, 8.82 s, 25H.

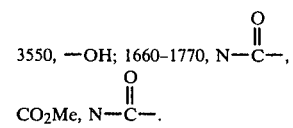

Mass Spec. Meas. mass, 487.3071; calc. mass, M$^+$, 487.3046.

PHARMACOLOGICAL DATA

Bronchodilation Activity

The compounds were examined for their ability to inhibit 5-hydroxytryptamine or histamine induced bronchoconstriction in the anaesthetised artificially respired guinea-pig (Konzett-Rossler preparation).

The ED$_{50}$ values (μg/kg, i.v.) for inhibition of bronchoconstriction for a variety of the triazolidine-3,5-diones are given in Table 7.

TABLE 7

| Compound | ED$_{50}$ μg/kg, i.v. |
|---|---|
| 29 | 2.6 |
| 31 | 37 |
| 32 | 0.74 |
| 33 | 2.6 |
| 43 | 1.9 |
| 21 | 3.4 |
| 24 | 4.0 |

Anti-platelet Aggregation Activity 1-(6'-ethoxycarbonyl-n-hexyl)-2-(3''-hydroxy-n-octyl)-4-phenyl-1,2,4-triazolidine-3,5-dione (21) inhibited collagen induced aggregation in human platelet rich plasma.

What we claim is:

1. A compound of the formula

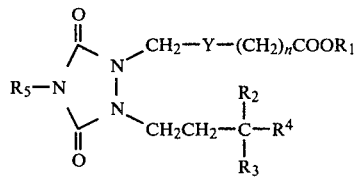

or a pharmaceutically acceptable salt thereof wherein n has a value of from 1 to 5;

Y is —CH$_2$CH$_2$— or —CH=CH—;

R$_1$ is hydrogen; alkyl of 1 to 12 carbon atoms; phenyl; or aralkyl of up to 12 carbon atoms;

R$_2$ when taken alone is hydrogen; alkyl of 1 to 4 carbon atoms; or phenyl;

R$_3$ is hydroxy or protected hydroxy;

R$_4$ when taken alone is hydrogen; alkyl of 1 to 9 carbon atoms; cycloalkyl of 3 to 8 carbon atoms; phenyl; naphthyl; or alkyl of 1 to 6 carbon atoms substituted with phenyl, naphthyl or cycloalkyl of 3 to 8 carbon atoms; any of said phenyl rings and said naphthyl rings being unsubstituted or substituted with halo, trifluoromethyl, alkyl of 1 to 6 carbon atoms, hydroxy, alkoxy of 1 to 6 carbon atoms, phenylalkoxy wherein alkoxy contains from 1 to 6 carbon atoms or nitro; $R_2$ and $R_4$ taken together, together with the carbon atom to which they are joined, are cycloalkylidene of 5 to 8 carbon atoms; and $R_5$ is hydrogen, alkyl of 1 to 6 carbon atoms, cycloalkyl of 5 to 8 carbon atoms; phenyl, alkyl of 1 to 6 carbon atoms substituted with phenyl or cycloalkyl of 3 to 8 carbon atoms substituted with phenyl, said phenyl rings being unsubstituted or substituted with halo, trifluoromethyl, alkyl of 1 to 6 carbon atoms, alkoxy of 1 to 6 carbon atoms or nitro.

2. A compound according to claim 1, wherein n is 2,3 or 4.

3. A compound according to claim 1 wherein $R_1$ is hydrogen or alkyl of 1 to 6 carbon atoms.

4. A compound according to claim 1 wherein $R_2$ is hydrogen, methyl or ethyl.

5. A compound according to claim 1 wherein $R_3$ is hydroxy.

6. A compound according to claim 1 wherein $R_4$ is alkyl of 4 to 9 carbon atoms.

7. A compound according to claim 1 wherein $R_5$ is alkyl of 1 to 6 carbon atoms.

8. A compound according to claim 1 wherein:
n is 2, 3, or 4;
$R_2$ is hydrogen, methyl, ethyl or unsubstituted phenyl;
$R_3$ is hydroxy;
$R_4$ is hydrogen or alkyl of 1 to 9 carbon atoms.

9. A compound according to claim 8 wherein $R_5$ is hydrogen, alkyl of 1 to 6 carbon atoms, unsubstituted phenyl or alkyl of 1 to 6 carbon atoms substituted with unsubstituted phenyl.

10. A compound according to claim 9 wherein $R_5$ is alkyl of 1 to 6 carbon atoms.

11. A compound according to claim 10 wherein $R_5$ is methyl.

12. A compound according to claim 9, wherein n is 3.

13. A compound according to claim 12 wherein $R_2$ is hydrogen or methyl.

14. A compound according to claim 13 wherein $R_4$ is n-pentyl, n-hexyl or n-heptyl.

15. A compound according to claim 13 wherein $R_4$ is hex-2-yl, hept-2-yl or oct-2-yl.

16. The compound according to claim 1 which is 1-(6-carbomethoxyhexyl)-2-(3,4-dimethyl-3-hydroxyoctyl)-4-methyl-1,2,4-triazolidine-3,5-dione.

17. A compound according to claim 1 wherein $R_5$ is hydrogen, alkyl of 1 to 6 carbon atoms, unsubstituted phenyl or alkyl of 1 to 6 carbon atoms substituted with unsubstituted phenyl.

18. A compound according to claim 1 wherein $R_3$ is hydroxy and $R_4$ is

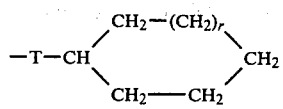

wherein T is a carbon-carbon bond or an alkylene chain which is straight or branched with one or two methyl groups and which has a total of 1 to 6 carbon atoms; and r has a value of from 0 to 3.

19. A compound according to claim 18 wherein $R_5$ is hydrogen, alkyl of 1 to 6 carbon atoms, unsubstituted phenyl or alkyl of 1 to 6 carbon atoms substituted with unsubstituted phenyl.

20. A compound according to claim 19 wherein $R_5$ is alkyl of 1 to 6 carbon atoms.

21. A compound according to claim 20 wherein $R_5$ is methyl.

22. A compound according to claim 19 wherein n is 3.

23. A compound according to claim 22 wherein $R_2$ is hydrogen or methyl.

24. A compound according to claim 19 wherein r is 1.

* * * * *